United States Patent
Ohmachi et al.

(10) Patent No.: US 10,376,543 B2
(45) Date of Patent: *Aug. 13, 2019

(54) FERMENTED MILK PRODUCT AND METHOD FOR PRODUCING THE SAME

(71) Applicant: MEGMILK SNOW BRAND CO., LTD., Hokkaido (JP)

(72) Inventors: Aiko Ohmachi, Saitama (JP); Hiroaki Matsuyama, Hokkaido (JP); Yoshikazu Morita, Hokkaido (JP); Yuko Ishida, Saitama (JP); Takayuki Nara, Hokkaido (JP); Ken Kato, Hokkaido (JP); Atsushi Serizawa, Hokkaido (JP); Hiroshi Ueno, Hokkaido (JP); Hiroshi Urazono, Saitama (JP)

(73) Assignee: MEGMILK SNOW BRAND CO., LTD., Hokkaido (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/450,596

(22) Filed: Mar. 6, 2017

(65) Prior Publication Data

US 2017/0173082 A1 Jun. 22, 2017

Related U.S. Application Data

(63) Continuation of application No. 14/418,285, filed as application No. PCT/JP2012/069396 on Jul. 31, 2012, now Pat. No. 9,629,878.

(51) Int. Cl.

| | | |
|---|---|---|
| *A61K 38/17* | (2006.01) |
| *A61K 35/20* | (2006.01) |
| *A23C 9/13* | (2006.01) |
| *A23L 2/38* | (2006.01) |
| *A23C 9/12* | (2006.01) |
| *A61K 38/44* | (2006.01) |
| *A61K 38/46* | (2006.01) |
| *A23C 9/146* | (2006.01) |

(52) U.S. Cl.
CPC ............ *A61K 35/20* (2013.01); *A23C 9/1213* (2013.01); *A23C 9/1307* (2013.01); *A23C 9/1315* (2013.01); *A23C 9/1322* (2013.01); *A23C 9/1465* (2013.01); *A23L 2/38* (2013.01); *A61K 38/443* (2013.01); *A61K 38/465* (2013.01); *A23V 2002/00* (2013.01); *C12Y 111/01007* (2013.01); *C12Y 301/27* (2013.01)

(58) Field of Classification Search
CPC ................................................ A61K 38/1709
See application file for complete search history.

(56) References Cited

U.S. PATENT DOCUMENTS

| | | | |
|---|---|---|---|
| 5,976,597 A | 2/1999 | Takada et al. |
| 5,932,259 A | 8/1999 | Kato et al. |
| 8,551,547 B2 | 10/2013 | Brown et al. |
| 2006/0228345 A1 | 10/2006 | Motouri et al. |
| 2010/0136172 A1 | 6/2010 | Brown et al. |
| 2011/0262422 A1 | 10/2011 | Cocks et al. |
| 2012/0040908 A1 | 2/2012 | Kido et al. |
| 2015/0182557 A1 | 7/2015 | Ohmachi et al. |
| 2015/0224178 A1 | 8/2015 | Ohmachi et al. |
| 2015/0297690 A1 | 10/2015 | Ohmachi et al. |
| 2015/0343029 A1 | 12/2015 | Ohmachi et al. |
| 2015/0343030 A1 | 12/2015 | Ohmachi et al. |

FOREIGN PATENT DOCUMENTS

| | | |
|---|---|---|
| EP | 0 704 218 | 4/1996 |
| JP | H06 - 135996 A | 5/1994 |
| JP | 8-151331 | 6/1996 |
| JP | H08-165249 A | 6/1996 |
| JP | H09-191858 A | 7/1997 |
| JP | 10-007585 | 1/1998 |
| JP | 2004-238320 | 8/2004 |
| JP | 2005-060321 | 3/2005 |
| JP | 2009-215301 | 9/2009 |
| JP | 2010 - 508827 A | 3/2010 |
| JP | 2011-519960 | 7/2011 |
| WO | 2010/058679 A | 5/2010 |

OTHER PUBLICATIONS

Japanese Office Action with English Translation in respect to Japanese Application No. 2017-035649, dated Mar. 7, 2018.
Morita et al., "Purification and identification of lactoperoxidase in milk basic proteins as an inhibitor of osteoclastogenesis," *Journal of Dairy Science*, vol. 94, No. 5, pp. 2270-2279, 2011.
International Search Report for PCT/JP2012/069396, dated Oct. 16, 2012.
International Preliminary Report on Patentability for PCT/JP2012/069396, dated Feb. 12, 2015.
Morita et al., "Identification of Angiogenin as the Osteoclastic Bone Resorption-Inhibitory Factor in Bovine Milk," *Bone*, vol. 42, pp. 380-387 (Oct. 4, 2007).
Search Report issued by European Patent Office (EPO) in related EPO Patent Application No. 12882143.6, dated Dec. 17, 2015.
Partial English-language translation of JP 2005-060321 (Mar. 10, 2005).

*Primary Examiner* — Rosanne Kosson
(74) *Attorney, Agent, or Firm* — Greenblum & Bernstein, P.L.C.

(57) ABSTRACT

The invention relates to provide a fermented milk product includes angiogenin and/or angiogenin hydrolysate in an amount of 0.9 mg/100 g to 150 mg/100 g, and lactoperoxidase and/or lactoperoxidase hydrolysate in the mass ratio to the angiogenin and/or angiogenin hydrolysate of 0.3 to 23.

10 Claims, No Drawings

FERMENTED MILK PRODUCT AND METHOD FOR PRODUCING THE SAME

CROSS-REFERENCE TO RELATED APPLICATIONS

This application is a Continuation of U.S. patent application Ser. No. 14/418,285, which is the National Stage of International Application No. PCT/JP2012/069396, filed Jul. 31, 2012. The disclosures of each of application Ser. No. 14/418,285 and PCT/JP2012/069396 are expressly incorporated by reference herein in their entireties.

TECHNICAL FIELD

This invention relates to a novel fermented milk product and a method for producing the same. The fermented milk product includes a specific milk component, and may be useful for prevention and treatment of various bone diseases such as osteoporosis, fracture, rheumatism, and arthritis.

BACKGROUND ART

In recent years, various bone diseases, such as osteoporosis, fracture, and backache have increased on a global basis along with aging of society and the like, and have become a serious social problem. These diseases are caused by insufficient calcium intake, depression of calcium absorption ability, hormone imbalance after menopause, and the like. It is considered that increase the body bone mass as much as possible by activating the osteoblast and bone formation from the early stage of life, and increase the maximum bone mass and the bone strength (bone density+bone quality) is effective in preventing various bone diseases, such as osteoporosis, fracture, and backache. Note that the term "bone quality" refers to the bone microstructure, metabolic turnover, microfracture, and calcification. It is thought that various bone diseases, such as osteoporosis, fracture, and backache may be prevented by suppressing osteoclastic bone resorption. Bones are repeatedly resorbed and formed in a balanced manner (remodeling). However, various bone diseases, such as osteoporosis, fracture, and backache may occur when bone resorption exceeds bone formation due to a change in hormone balance after menopause, and the like. Therefore, bones can be strengthened by suppressing osteoclastic bone resorption and maintaining the bone strength at a constant level.

In view of the above situation, a drug, food, drink, feed, or the like in which a calcium salt, such as calcium carbonate, calcium phosphate, or calcium lactate or a natural calcium product, such as whey calcium, bovine bone powder, or eggshell is added individually, has been administered in order to strengthen bones. A drug, food, drink, feed, or the like that contains such a calcium product together with a substance having a calcium absorption-promoting effect, such as casein phosphopeptide or oligosaccharide has also been used to strengthen bones. However, the calcium absorption rate is 50% or less, when a food or drink that contains a calcium salt or a natural calcium product is administered, and the large part of the calcium administered may be discharged from the body without being absorbed. Moreover, even if calcium is absorbed into the body, it does not necessarily exhibit the bone metabolism-improving effect or a bone-strengthening effect, since the affinity to bones may differ according to its form or the type of nutritional ingredient administered together, An estrogen product, an active vitamin $D_3$ product, a vitamin $K_2$ product, a bisphosphonate product, a calcitonin product, and the like have been known as a drug for treating osteoporosis or strengthening bones, and new drugs such as an anti-RANKL antibody have been also developed. However, these drugs may have side effects such as buzzing in the ear, a headache, or loss of appetite. Moreover, the above substances are in a situation that they cannot be added to a food or drink at present from the viewpoint of safety, cost, and the like. Therefore, in light of the nature of various bone diseases, such as osteoporosis, fracture, and backache, development of such a food or drink that can be administered orally for a long time, increases the bone strength by promoting bone formation and suppressing bone resorption, and may be expected to have the effect of preventing or treating the various bone diseases has been desired.

PRIOR-ART DOCUMENT

Patent Document

[Patent Document 1] JP-A-H08-151331
[Patent Document 2] JP-A-H10-7585
[Patent Document 3] JP-A-2004-238320
[Patent Document 4] JP-A-2005-60321

SUMMARY OF THE INVENTION

Problems to be Solved by the Invention

The invention relates to provide a fermented milk product that may be useful for prevention and treatment of various bone diseases such as osteoporosis, fracture, rheumatism, and arthritis.

Means for Solving the Problems

The present inventors have found that the bone density can be effectively increased by taking a fermented milk product that includes angiogenin and/or angiogenin hydrolysate, and includes lactoperoxidase and/or lactoperoxodase hydrolysate in a specific mass ratio with respect to angiogenin and/or angiogenin hydrolysate. This finding has led to the completion of the invention.

Specifically, the invention includes following aspects:

(1) A fermented milk product including angiogenin and/or angiogenin hydrolysate in an amount of 0.9 mg/100 g to 150 mg/100 g and lactoperoxidase and/or lactoperoxodase hydrolysate in the mass ratio to the angiogenin and/or angiogenin hydrolysate of 0.3 to 23.

(2) A method of preventing bone diseases including administering the fermented milk product according to (1) in an amount of 100 g/day or more.

(3) A method of producing the fermented milk product according to (1), including mixing angiogenin and/or angiogenin hydrolysate and lactoperoxidase and/or lactoperoxodase hydrolysate with a milk product raw material and sterilized the obtained mixture, and then fermented.

(4) A method of producing the fermented milk product according to (1), including adding angiogenin and/or angiogenin hydrolysate and lactoperoxidase and/or lactoperoxodase hydrolysate to a sterilized milk raw material.

Effects of the Invention

The fermented milk product of the invention exhibits a bone-strengthening effect, and may be useful for prevention and treatment of various bone diseases such as osteoporosis, fracture, rheumatism, and arthritis.

DETAILED DESCRIPTION OF THE INVENTION

A fermented milk product of the invention is characterized in that the fermented milk product includes angiogenin and/or angiogenin hydrolysate in a specific amount, and further includes lactoperoxidase and/or lactoperoxodase hydrolysate in a specific mass ratio with respect to angiogenin and/or angiogenin hydrolysate.

A fermented milk product generally contains angiogenin and/or angiogenin hydrolysate in an amount of about 0.2 to 0.8 mg/100 g, and lactoperoxidase and/or lactoperoxodase hydrolysate in an amount of about 1.2 to 6.8 mg/100 g.

In contrast, the fermented milk product of the invention is added with angiogenin and/or angiogenin hydrolysate and lactoperoxidase and/or lactoperoxodase hydrolysate, and the fermented milk product contains angiogenin and/or angiogenin hydrolysate in an amount of 0.9 mg/100 g to 150 mg/100 g, and lactoperoxidase and/or lactoperoxodase hydrolysate in a mass ratio with respect to angiogenin and/or angiogenin hydrolysate of 0.3 to 23.

A fraction containing angiogenin and/or angiogenin hydrolysate that is prepared from milk of a mammal, such as human, cow, buffalo, goat, or sheep, a fraction containing lactoperoxidase and/or lactoperoxodase hydrolysate that is prepared from milk of a mammal, such as human, cow, buffalo, goat, or sheep, a fraction containing angiogenin and/or angiogenin hydrolysate that is produced by a genetic engineering, a fraction containing lactoperoxidase and/or lactoperoxodase hydrolysate that is produced by a genetic engineering, angiogenin and/or angiogenin hydrolysate purified from blood or an organ, lactoperoxidase and/or lactoperoxodase hydrolysate purified from blood or an organ, or the like may be used as the angiogenin and/or angiogenin hydrolysate and the lactoperoxidase and/or lactoperoxodase hydrolysate included in the fermented milk product of the invention. A commercially available purified angiogenin or lactoperoxidase reagent may also be used.

The fermented milk product of the invention may include angiogenin hydrolysate or lactoperoxodase hydrolysate obtained by digesting a fraction containing angiogenin, an angiogenin reagent, a fraction containing lactoperoxidase, a lactoperoxidase reagent, or the like using one or more proteases.

The fermented milk product of the invention may include a protein material prepared by extracting a fraction containing angiogenin and/or angiogenin hydrolysate and lactoperoxidase and/or lactoperoxodase hydrolysate directly from milk or a material derived from milk, such as skim milk or whey. Such a protein material may be prepared as follows, for example. Specifically, milk or a material derived from milk is brought into contact with a cation-exchange resin, and milk-derived proteins adsorbed on the resin is eluted at a salt concentration of 0.1 to 2.0 M, desalted and concentrated using a reverse osmosis membrane, an electrodialysis membrane, an ultrafiltration membrane, a microfiltration membrane, or the like, and optionally subjected to proteolysis to a molecular weight of 8000 or less using a protease, such as trypsin, pancreatin, chymotrypsin, pepsin, papain, kallikrein, cathepsin, thermolysin, or V8 protease. When subjecting to proteolysis using a protease, the lower limit of the molecular weight is preferably 500 or more. The protein material thus obtained may be dried by freeze-drying, spray drying, or the like, and the dried product may be added in the fermented milk product.

The fermented milk product of the invention is produced by adding angiogenin and/or angiogenin hydrolysate, and lactoperoxidase and/or lactoperoxodase hydrolysate and a protein material that contains angiogenin and/or angiogenin hydrolysate and lactoperoxidase and/or lactoperoxodase hydrolysate, or the like to a fermented milk product raw material so that the fermented milk product includes angiogenin and/or angiogenin hydrolysate in an amount of 0.9 mg/100 g to 150 mg/100 g, and includes lactoperoxidase and/or lactoperoxodase hydrolysate in a mass ratio with respect to angiogenin and/or angiogenin hydrolysate of 0.3 to 23.

As shown in the test examples described below, when the fermented milk product includes angiogenin and/or angiogenin hydrolysate and lactoperoxidase and/or lactoperoxodase hydrolysate as described above, the bone-strengthening effect can be obtained more effectively than the case of taking angiogenin and/or angiogenin hydrolysate or lactoperoxidase and/or lactoperoxodase hydrolysate separately.

The fermented milk product of the invention may be produced in the usual manner as long as the fermented milk product includes the angiogenin and/or angiogenin hydrolysate and lactoperoxidase and/or lactoperoxodase hydrolysate in specific amounts, respectively. The fermented milk product produced according to the invention may include all fermented milk product, such as a fermented milk product, a dairy lactic acid bacteria beverage, a lactic acid bacteria beverage, and the like. For example, the fermented milk product of the invention is produced by optionally mixing a milk raw material, adding angiogenin and/or angiogenin hydrolysate thereto so that the fermented milk product includes angiogenin and/or angiogenin hydrolysate in a specific amount, and adding lactoperoxidase and/or lactoperoxodase hydrolysate to the mixture so that the fermented milk product includes lactoperoxidase and/or lactoperoxodase hydrolysate in the specific range of the mass ratio to angiogenin and/or angiogenin hydrolysate. Note that as the milk raw material, cow milk, concentrated skim milk, skim milk powder, whey, butter, cream, or the like, in addition to a milk-based drink, processed milk, composition-modified milk, low-fat milk, fat-free milk, or the like that is obtained by appropriately or optionally mixed the above cow milk, concentrated skim milk, skim milk powder, whey, butter, cream, or the like can be given, for example. After that, An appropriate amount of a starter culture prepared from lactic acid bacteria such as *Lactobacillus bulgaricus, Streptococcus thermophilus, Lactobacillus helveticus, Lactobacillus acidophilus*, or *Lactobacillus kefiri*, or yeast such as *Kluyveromyces marxianus* or *Saccharomyces unisporus* is added to the milk raw material, and the resulting mixture is fermented in the usual manner to prepare a fermented milk product of the invention.

When adding angiogenin and/or angiogenin hydrolysate and lactoperoxidase and/or lactoperoxodase hydrolysate to a milk raw material, angiogenin and/or angiogenin hydrolysate and lactoperoxidase and/or lactoperoxodase hydrolysate may be added to either unsterilized milk raw material, or a sterilized milk raw material. When adding to an unsterilized milk raw material, sterilization may be conducted after the addition. In this instance, heat sterilization is preferable. When sterilizing the mixture after mixing the angiogenin and/or angiogenin hydrolysate and lactoperoxidase and/or lactoperoxodase hydrolysate with the milk raw material, it is preferable to sterilize the mixture at 130° C. for 2 seconds or less.

It may be possible that the fermented milk product of the invention may be added with a raw material or the like that is commonly used for a food or drink, such as a saccharide, a lipid, a protein, a vitamin, a mineral, or a flavor, in addition to angiogenin and/or angiogenin hydrolysate, lactoperoxidase and/or lactoperoxodase hydrolysate, other than the above milk raw material, and may also be added with another bone-strengthening component such as calcium, vitamin D, vitamin K, or isoflavone.

The fermented milk product of the invention can strengthen bones when administered orally in an amount of 100 g or more per kg of body weight, as shown in the animal experiments described below. Since the intake for the experiment animal corresponds to the intake for adults in terms of blood drug concentration (see Mitsuyoshi Nakajima (1993), "Yakkou Hyoka Vol. 8", Hirokawa-Shoten Ltd., pp. 2-18), it is expected that bones can be strengthened, and especially various bone diseases, such as osteoporosis, fracture, rheumatism, and arthritis can be prevented or treated by ingesting the fermented milk product of the invention in an amount of 100 g/day or more per adult.

The invention is further described below in more detail by way of reference examples, examples, and test examples. Note that the following examples are intended for illustration purposes only, and should not be construed as limiting the invention.

Reference Example 1

Preparation (1) of Angiogenin Fraction

A column filled with 30 kg of cation-exchange resin (Sulfonated Chitopearl; manufactured by Fuji Spinning Co., Ltd.) was thoroughly washed with deionized water, and 1000 liters of unpasteurized skim milk (pH 6.7) was then applied to the column. After thoroughly washing the column with deionized water, the absorbed protein was eluted with a linear gradient of 0.1 to 2.0 M sodium chloride. The eluted fraction containing angiogenin was fractionated using an S-Sepharose cation-exchange chromatography (manufactured by Amersham Bio scientific), and the resulted angiogenin-containing fraction was heat-treated at 90° C. for 10 minutes, and centrifuged to remove a precipitate. The angiogenin-containing fraction was further subjected to gel filtration chromatography (column: Superose 12). The eluate obtained was desalted using a reverse osmosis membrane, and the desalted eluate was freeze-dried to obtain 16.5 g of an angiogenin fraction having an angiogenin purity of 90%. These successive operations were repeated 30 times.

Reference Example 2

Preparation (2) of Angiogenin Fraction

A column filled with 10 kg of Heparin Sepharose (manufactured by GE Healthcare) was thoroughly washed with deionized water, and 500 liters of unpasteurized skim milk (pH 6.7) was then applied to the column. After thoroughly wash the column with a 0.5 M sodium chloride solution, the absorbed protein was eluted with a 1.5 M sodium chloride solution. The eluate was desalted using a reverse osmosis membrane, and the desalted eluate was freeze-dried to obtain 18 g of an angiogenin fraction having an angiogenin purity of 5%. The above successive operations were repeated 50 times.

Reference Example 3

Preparation of Lactoperoxidase Fraction

A column (diameter: 5 cm, height: 30 cm) filled with 600 g of cation-exchange resin (sulfonated Chitopearl; manufactured by Fuji Spinning Co., Ltd.) was thoroughly washed with deionized water, and 360 liters of unpasteurized skim milk (pH 6.7) was applied to the column at a flow rate of 25 ml/min. After thoroughly wash the column with deionized water, the absorbed protein was eluted with a 0.02 M carbonate buffer (pH 7.0) containing 2.0 M sodium chloride. The eluted fraction containing lactoperoxidase was adsorbed on an S-Sepharose FF column (manufactured by Amersham Bioscientific), and the column was thoroughly washed with deionized water. After equilibration with a 10 mM phosphate buffer (pH 7.0), the adsorbed fraction was eluted with a linear gradient of 0 to 2.0 M sodium chloride to collect a fraction containing lactoperoxidase. The fraction was subjected to gel filtration chromatography using a HiLoad 16/60 Superdex 75pg (manufactured by Amersham Bioscientific). The eluate obtained was desalted using a reverse osmosis membrane, and freeze-dried to obtain 27 g of a lactoperoxidase fraction having a lactoperoxidase purity of 90%. These successive operations were repeated 25 times.

Measurement of Angiogenin and Lactoperoxidase Contained in Fermented Milk Product The content of angiogenin, angiogenin hydrolysate, lactoperoxidase and lactoperoxodase hydrolysate in the fermented milk product was measured according to the method described in JP-A-2008-164511 with modification. Specifically, 86 µl of the fermented milk product was added to 5 ml of ultrapure water, and a 1/1000-equivalent amount of formic acid was added to the mixture to prepare a sample solution. Ten microliter (10 µl) of the sample solution was dried up, and dissolved in 20 µl of 0.1 M ammonium bicarbonate containing 8 M urea and 1 mM tris(carboxyethyl)phosphine (TCEP). The solution was heated at 56° C. for 30 minutes. After returning the solution to room temperature, 5 µl of 100 mM iodoacetamide solution was added to the solution, and the mixture was reacted for 30 minutes in the dark. After the addition of 54 µl of ultrapure water, 10 µl of 0.1 µg/ml trypsin and 10 µl of 0.1 µg/ml Lysyl Endopeptidase were added to the mixture. The mixture was reacted at 37° C. for 16 hours. The reaction was then terminated by adding 3 µl of formic acid and used as the sample peptide solution for measurement. The sample solution was diluted 6-fold with 10 fmol/µl internal standard peptide solution containing 0.1% formic acid, 0.02% trifluoroacetic acid (TFA), and 2% acetonitril, and 2.5 µl of the diluted solution was subjected to LC/MS/MS analysis.

The peptides were separated by gradient elution using an HPLC system. More specifically, the peptides were separated using a column (MAGIC C18, 0.2 mm (ID)×50 mm) equipped with a 5 µl-peptide trap on a MAGIC 2002 HPLC system at a flow rate of 2 µl/min. A solution A (2% acetonitrile-0.05% formic acid) and a solution B (90% acetonitrile-0.05% formic acid) were used as eluant for HPLC. Gradient elution was conducted under the elution condition from 2 to 65% the solution B over 20 minutes.

As object ions for measuring lactoperoxidase, parent ion was $NH_2$-IHGFDLAAINLQR-COOH (m/z 734.4), and the MS/MS target ion was $NH_2$-IHGFDLA-COOH (m/z 754.4). As object ions for measuring angiogenin, parent ion was $NH_2$-YIHFLTQHYDAK-COOH (m/z 768.8), and the MS/MS target ion was $NH_2$-FLTQHYDAK-COOH (m/z 1122.8). Regarding the internal standard peptide parent ion was $NH_2$-ETTVFENLPEK-COOH (wherein, P was labeled with $^{13}C$ and $^{15}N$) (m/z 656.9.), and the MS/MS target ion was $NH_2$-FENLPEK-COOH (wherein, P was labeled with $^{13}C$ and $^{15}N$) (m/z 882.4).

A system "LCQ Advantage" was used for MS. The peak area of each protein was calculated from the resulting chromatogram, and the concentration was calculated from the ratio with respect to the internal standard peptide.

Example 1

One hundred and sixty six milligrams (166 mg) of the angiogenin fraction obtained in Reference Example 1 and 0.4 mg of the lactoperoxidase fraction obtained in Reference Example 3 were mixed with 100 g of a mixture prepared by adding a starter culture to a 10% reduced skim milk powder that had been sterilized at 100° C. for 10 minutes, the resulting mixture was fermented in the usual manner to obtain a fermented milk product (example product 1). The obtained fermented milk product contained angiogenin and/or angiogenin hydrolysate in an amount of 150 mg/100 g, and the mass ratio of lactoperoxidase and/or lactoperoxodase hydrolysate to angiogenin and/or angiogenin hydrolysate in the fermented milk product was 0.3.

Example 2

Twelve milligrams (12 mg) of the angiogenin fraction obtained in Reference Example 2 and 18 mg of the lactoperoxidase fraction obtained in Reference Example 3 were mixed with 100 g of a mixture prepared by adding a starter culture to a 10% reduced skim milk powder that had been sterilized at 100° C. for 10 minutes, and the resulting mixture was fermented in the usual manner to obtain a fermented milk product (example product 2). The obtained fermented milk product contained angiogenin and/or angiogenin hydrolysate in an amount of 0.9 mg/100 g, and the mass ratio of lactoperoxidase and/or lactoperoxodase hydrolysate to angiogenin and/or angiogenin hydrolysate in the fermented milk product was 23.

Example 3

Twelve milligrams (12 mg) of the angiogenin fraction obtained in Reference Example 1 and 18 mg of the lactoperoxidase fraction obtained in Reference Example 3 were mixed with 100 g of a mixture prepared by adding a starter culture to a 10% reduced skim milk powder that had been sterilized at 100° C. for 10 minutes, and the resulting mixture was fermented in the usual manner to obtain a fermented milk product (example product 3). The obtained fermented milk product contained angiogenin and/or angiogenin hydrolysate in an amount of 11 mg/100 g, and the mass ratio of lactoperoxidase and/or lactoperoxodase hydrolysate to angiogenin and/or angiogenin hydrolysate in the fermented milk product was 1.9.

Comparative Example 1

Eight milligrams (8 mg) of the angiogenin fraction obtained in Reference Example 2 and 22 mg of the lactoperoxidase fraction obtained in Reference Example 3 were mixed with 100 g of a mixture prepared by adding a starter culture to a 10% reduced skim milk powder that had been sterilized at 100° C. for 10 minutes, and the resulting mixture was fermented in the usual manner to obtain a fermented milk product (comparative example product 1). The obtained fermented milk product contained angiogenin and/or angiogenin hydrolysate in an amount of 0.9 mg/100 g, and the mass ratio of lactoperoxidase and/or lactoperoxodase hydrolysate to angiogenin and/or angiogenin hydrolysate in the fermented milk product was 27.

Comparative Example 2

One hundred and seventy five milligrams (175 mg) of the angiogenin fraction obtained in Reference Example 1 and 30 mg of the lactoperoxidase fraction obtained in Reference Example 3 were mixed with 100 g of a mixture prepared by adding a starter culture to a 10% reduced skim milk powder that had been sterilized at 100° C. for 10 minutes, and the resulting mixture was fermented in the usual manner to obtain a fermented milk product (comparative example product 2). The obtained fermented milk product contained angiogenin and/or angiogenin hydrolysate in an amount of 158 mg/100 g, and the mass ratio of lactoperoxidase and/or lactoperoxodase hydrolysate to angiogenin and/or angiogenin hydrolysate in the fermented milk product was 0.2.

Test Example 1

The bone-strengthening effects of the example products 1 to 3 and the comparative example products 1 and 2 were determined by animal experiments. C3H/HeJ mice (5 weeks old, male) were used for the animal experiments. After 1 week acclimation, the mice were divided into six groups (10 mice/group). The mice were orally administered each product of the example products 1 to 3 and the comparative example products 1 and 2 in an amount of 100 g per 1 kg of mouse weight once a day for 2 weeks using a tube. The control group was not administrated any example products 1 to 3 and the comparative example products 1 and 2. After completion of administration (second week), the bone density of the right tibia of each mouse was measured using a micro-CT (manufactured by Rigaku Corporation). The results are shown in Table 1. As shown in Table 1, the groups that were orally administered the example products 1 to 3 showed a significant increase in bone density compared with the control group and the comparative example groups that were orally administered the comparative example product 1 or 2.

TABLE 1

|  | Bone density (mg/cm$^3$) |
| --- | --- |
| Control group | 1241 ± 9 |
| Example product 1 | 1264 ± 13 |
| Example product 2 | 1272 ± 11 |
| Example product 3 | 1267 ± 10 |
| Comparative example product 1 | 1246 ± 7 |
| Comparative example product 2 | 1245 ± 5 |

Reference Example 4

A column (diameter: 4 cm, height: 30 cm) filled with 400 g of cation-exchange resin (Sulfonated Chitopearl; manufactured by Fuji Spinning Co., Ltd.) was thoroughly washed with deionized water, and 40 liters of unpasteurized skim milk (pH 6.7) was applied to the column at a flow rate of 25 ml/min. After thoroughly washing the column with deionized water, proteins adsorbed on the resin were eluted using a 0.02 M carbonate buffer (pH 7.0) containing 0.78 M sodium chloride. The eluate was desalted using a reverse osmosis membrane, and the desalted eluate was freeze-dried to obtain 18 g of a powdery protein material (reference example product 4).

Reference Example 5

Four grams (4 g) of protein material of the reference example product 4 was dissolved in 800 ml of water. After the addition of trypsin (manufactured by Sigma), which is a protease, at the final concentration of 0.03 wt %, the mixture was subjected to enzymatic treatment at 37° C. for 8 hours. After inactivating the protease through heat-treatment at 90°

C. for 5 minutes, the mixture was freeze-dried to obtain 3.0 g of a powdery protein material (reference example product 5).

Example 4

Forty milligrams (40 mg) of the reference example product 4 was mixed with 97 g of a 10% reduced skim milk powder, and the mixture was sterilized at 93° C. for 6 minutes, followed by adding 3 g of a starter culture, the resulting mixture was fermented in the usual manner to obtain a fermented milk product (example product 4). The obtained fermented milk product contained angiogenin and/or angiogenin hydrolysate in an amount of 2.4 mg/100 g, and the mass ratio of lactoperoxidase and/or lactoperoxodase hydrolysate to angiogenin and/or angiogenin hydrolysate in the fermented milk product was 5.4.

Example 5

Forty milligrams (40 mg) of the reference example product 5 was mixed with 97 g of a 10% reduced skim milk powder, and the mixture was sterilized at 93° C. for 6 minutes, followed by adding 3 g of a starter culture, the mixture was fermented in the usual manner to obtain a fermented milk product (example product 5). The obtained fermented milk product contained angiogenin and/or angiogenin hydrolysate in an amount of 2.3 mg/100 g, and the mass ratio of lactoperoxidase and/or lactoperoxodase hydrolysate to angiogenin and/or angiogenin hydrolysate in the fermented milk product was 5.3.

Comparative Example 3

Fifteen milligrams (15 mg) of the reference example product 4 and 25 mg of the lactoperoxidase fraction obtained in Reference Example 3 were mixed with 97 g of a 10% reduced skim milk powder, and the mixture was sterilized at 93° C. for 6 minutes, followed by adding 3 g of a starter culture, the resulting mixture was fermented in the usual manner to obtain a fermented milk product (comparative example product 3). The obtained fermented milk product contained angiogenin and/or angiogenin hydrolysate in an amount of 1.2 mg/100 g, and the mass ratio of lactoperoxidase and/or lactoperoxodase hydrolysate to angiogenin and/or angiogenin hydrolysate in the fermented milk product was 27

Test Example 2

The bone-strengthening effects of the example products 4 and 5 and the comparative example product 3 was determined by animal experiments. Forty SD female rats (51 weeks old) were used for the animal experiments. The rats were divided into five groups (8 rats/group). Four groups underwent ovariectomy, and the remaining one group sham surgery. After a 4-week recovery period, the ovariectomized rats were orally administered the example products 4 or 5 or the comparative example product 3 in an amount of 100 g per 1 kg of rat weight daily in six divided dose for 16 weeks using a tube. The control group was not administrated any example products 4 and 5 and the comparative example product 3. After 4-week recovery period, the rats underwent sham surgery were fed for 16 weeks in the same manner as the control group. After completion of administration (six-teenth week), the bone density of the right tibia of each rat was measured using a micro-CT (manufactured by Rigaku Corporation).

The results are shown in Table 2. As shown in Table 2, the groups that were orally administered the example products 4 and 5 showed a significant increase in bone density as compared with the control group and the group that was orally administered the comparative example product 3. Moreover, the bone density approached that of the sham surgery group.

TABLE 2

| | Bone density (mg/cm³) |
| --- | --- |
| Control group | 550 ± 10 |
| Sham surgery group | 603 ± 9 |
| Example product 4 | 598 ± 13 |
| Example product 5 | 594 ± 10 |
| Comparative example product 3 | 554 ± 8 |

Example 6

Fifty milligrams (50 mg) of the reference example product 4 was mixed with 98 g of 2.5% reduced skim milk powder that had been sterilized at 100° C. for 10 minutes, followed by adding 2 g of a starter culture, the resulting mixture was fermented in the usual manner, sterilized at 130° C. for 2 seconds, and cooled to 10° C. to obtain a fermented milk product (example product 6). The obtained fermented milk product contained angiogenin and/or angiogenin hydrolysate in an amount of 2.9 mg/100 g, and the mass ratio of lactoperoxidase and/or lactoperoxodase hydrolysate to angiogenin and/or angiogenin hydrolysate in the fermented milk product was 5.2.

What is claimed is:

1. A fermented milk product comprising angiogenin and/or angiogenin hydrolysate in an amount of 0.9 mg/100 g to 150 mg/100 g and lactoperoxidase and/or lactoperoxidase hydrolysate in the mass ratio to the angiogenin and/or angiogenin hydrolysate of 0.3:1 to 23:1, wherein the fermented milk product is obtained by fermenting a composition comprising (i) a starter culture added to skim milk or to a reconstituted skim milk obtained by dissolving skim milk powder, (ii) an angiogenin fraction, and (iii) a lactoperoxidase fraction.

2. The fermented milk product of claim 1, which is a lactic acid bacteria beverage or food.

3. The fermented milk product of claim 2, which is a dairy lactic acid bacteria beverage.

4. A food, drink, or feed comprising a fermented milk product comprising angiogenin and/or angiogenin hydrolysate in an amount of 0.9 mg/100 g to 150 mg/100 g and lactoperoxidase and/or lactoperoxidase hydrolysate in the mass ratio to the angiogenin and/or angiogenin hydrolysate of 0.3:1 to 23:1, wherein the fermented milk product is obtained by fermenting a composition comprising (i) a starter culture added to skim milk or to a reconstituted skim milk obtained by dissolving skim milk powder, (ii) an angiogenin fraction, and (iii) a lactoperoxidase fraction.

5. A method of producing the fermented milk product according to claim 1, comprising mixing angiogenin and/or angiogenin hydrolysate with lactoperoxidase and/or lactoperoxidase hydrolysate and with a milk product raw material, sterilizing the obtained mixture, and then fermenting the mixture.

6. A method of producing the fermented milk product according to claim 1, comprising adding angiogenin and/or angiogenin hydrolysate and lactoperoxidase and/or lactoperoxidase hydrolysate to a sterilized milk product raw material.

7. The fermented milk product of claim 1, wherein at least one of the angiogenin and the lactoperoxidase is in the form of the hydrolysate thereof.

8. The fermented milk product of claim 2, wherein at least one of the angiogenin and the lactoperoxidase is in the form of the hydrolysate thereof.

9. The fermented milk product of claim 3, wherein at least one of the angiogenin and the lactoperoxidase is in the form of the hydrolysate thereof.

10. The food, drink, or feed of claim 4, wherein at least one of the angiogenin and the lactoperoxidase is in the form of the hydrolysate thereof.

\* \* \* \* \*